(12) United States Patent
Ohara

(10) Patent No.: US 10,478,053 B2
(45) Date of Patent: Nov. 19, 2019

(54) ENDOSCOPE ILLUMINATION DEVICE

(71) Applicant: OLYMPUS CORPORATION, Tokyo (JP)

(72) Inventor: Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 53 days.

(21) Appl. No.: 15/947,176

(22) Filed: Apr. 6, 2018

(65) Prior Publication Data

US 2018/0228353 A1    Aug. 16, 2018

Related U.S. Application Data

(63) Continuation of application No. PCT/JP2015/078520, filed on Oct. 7, 2015.

(51) Int. Cl.
*A61B 1/06* (2006.01)
*A61B 1/07* (2006.01)
(Continued)

(52) U.S. Cl.
CPC .......... *A61B 1/0653* (2013.01); *A61B 1/0638* (2013.01); *A61B 1/0661* (2013.01);
(Continued)

(58) Field of Classification Search
CPC ..... A61B 1/043; A61B 1/0638; A61B 1/0653; A61B 1/0661; A61B 1/0684; A61B 1/07;
(Continued)

(56) References Cited

U.S. PATENT DOCUMENTS 4,666,246 A * 5/1987 Nishioka ............ G02B 23/2469
                                              385/117
5,800,343 A * 9/1998 Takeuchi ................. A61B 1/07
                                              600/132
(Continued)

FOREIGN PATENT DOCUMENTS

JP       2011123368 A     6/2011
JP       2012074241 A     4/2012
(Continued)

OTHER PUBLICATIONS

Japanese Office Action dated Apr. 9, 2019 in Japanese Patent Application No. 2017-544199.
(Continued)

*Primary Examiner* — Nathnael Aynalem
(74) *Attorney, Agent, or Firm* — Scully, Scott, Murphy & Presser, P.C.

(57) ABSTRACT

An endoscope illumination device includes a light source that outputs primary light, a light guide that includes a first end face from which the primary light is radiated, and guides the primary light, and a light converter that is disposed to face the first end face, includes a second end face which the primary light enters, converts part of the primary light into secondary light. The illumination device also includes a holder that holds the light guide and the light converter so that an incident angle of the secondary light that is radiated from a point of intersection of the second end face and an optical axis of the light guide on the first end face and enters the first end face is equal to or larger than an acceptance angle (NA) of the light guide.

24 Claims, 11 Drawing Sheets

(51) Int. Cl.
  *G02B 6/02* (2006.01)
  *F21V 8/00* (2006.01)
  *A61B 1/04* (2006.01)
  *G01N 21/64* (2006.01)
  *G02B 6/42* (2006.01)

(52) U.S. Cl.
  CPC .............. *A61B 1/07* (2013.01); *G02B 6/0008* (2013.01); *G02B 6/02* (2013.01); *G02B 6/02038* (2013.01); *A61B 1/043* (2013.01); *A61B 1/0684* (2013.01); *G01N 21/6456* (2013.01); *G01N 2021/6484* (2013.01); *G01N 2201/0612* (2013.01); *G02B 6/4296* (2013.01)

(58) Field of Classification Search
  CPC ....... G01N 2021/6484; G01N 21/6456; G01N 2201/0612; G02B 6/0008; G02B 6/02; G02B 6/02038; G02B 6/4296
  USPC ...................................... 348/45, 68
  See application file for complete search history.

(56) References Cited

U.S. PATENT DOCUMENTS

| | | | | |
|---|---|---|---|---|
| 7,340,131 B2 * | 3/2008 | Nakama | ............... | G02B 6/2937 385/27 |
| 2010/0080016 A1 * | 4/2010 | Fukui | ................... | A61B 1/0653 362/574 |
| 2015/0078031 A1 * | 3/2015 | Komazaki | ............ | A61B 1/0653 362/583 |

FOREIGN PATENT DOCUMENTS

| | | |
|---|---|---|
| JP | 5103874 B2 | 12/2012 |
| JP | 2013004208 A | 1/2013 |
| JP | 2013104812 A | 5/2013 |
| JP | 2013165749 A | 8/2013 |
| JP | 2014174192 A | 9/2014 |
| JP | 2015019013 A | 1/2015 |

OTHER PUBLICATIONS

English translation of International Preliminary Report on Patentability dated Apr. 19, 2017 together with the Written Opinion received in related International Application No. PCT/JP2015/078520.

International Search Report dated Dec. 22, 2015 issued in PCT/JP2015/078520.

Abstract only of JP 2008-122838 A.

* cited by examiner

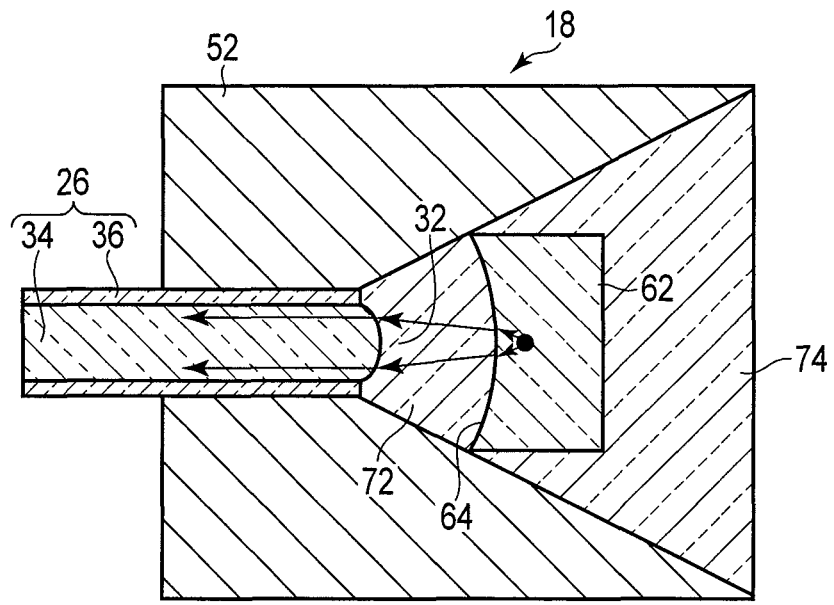
F I G. 5
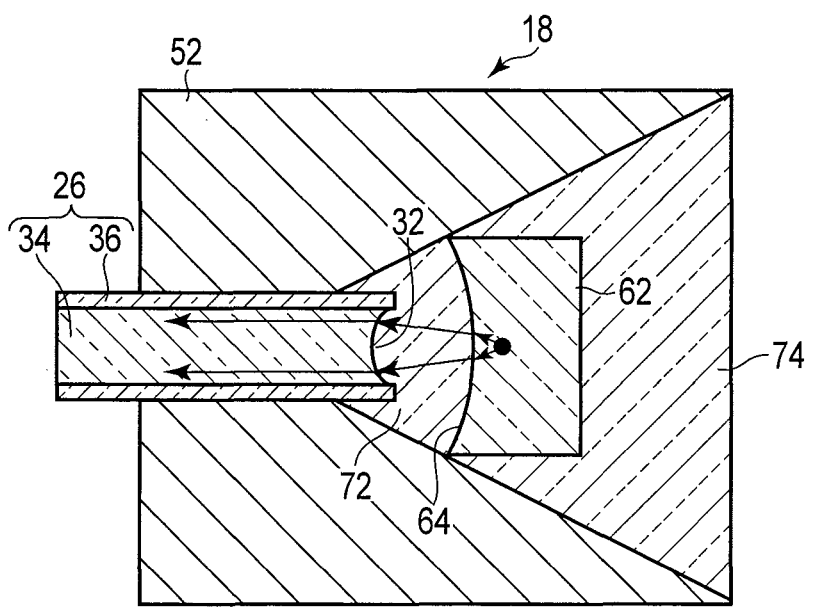
F I G. 6

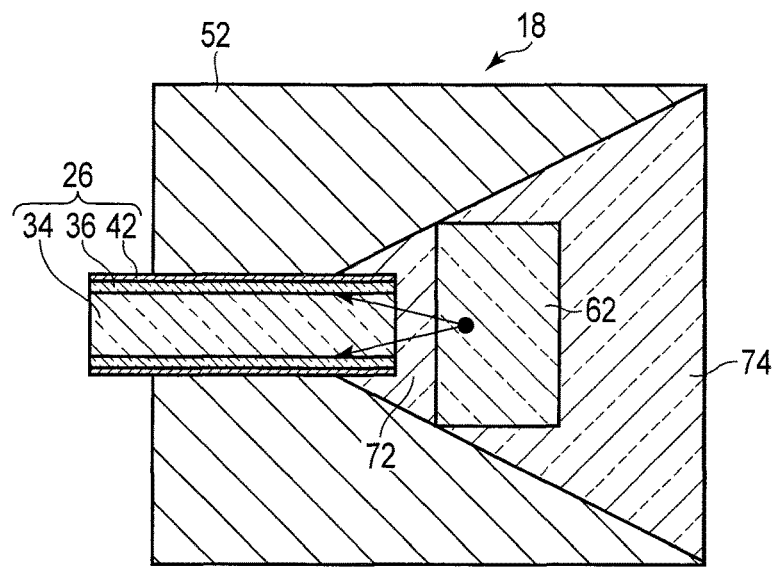
F I G. 9
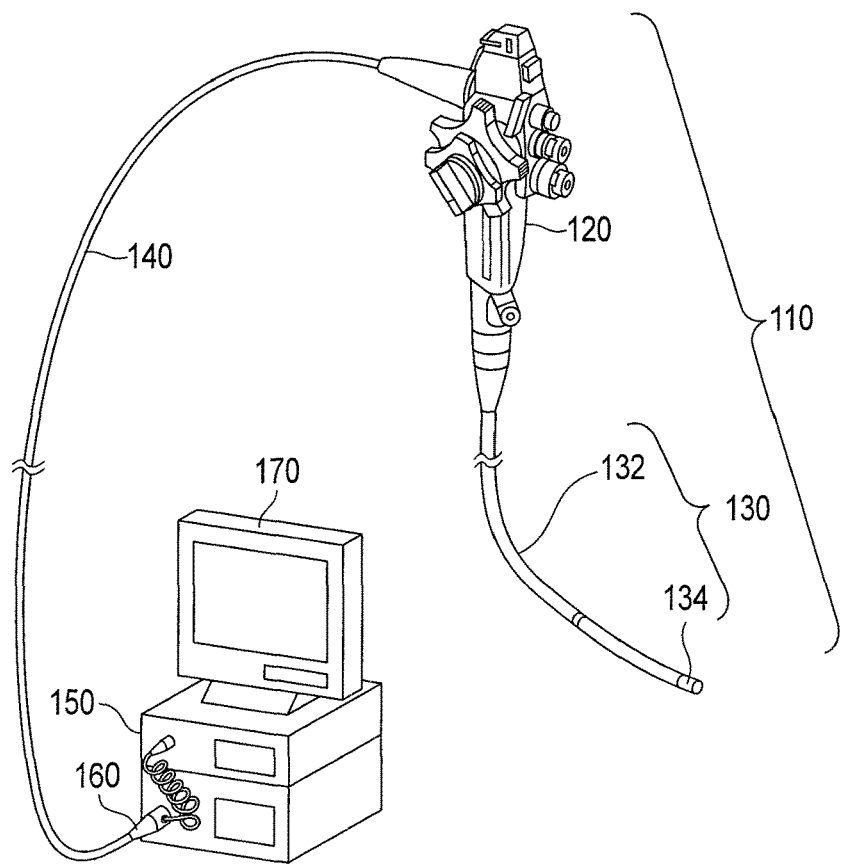
F I G. 10

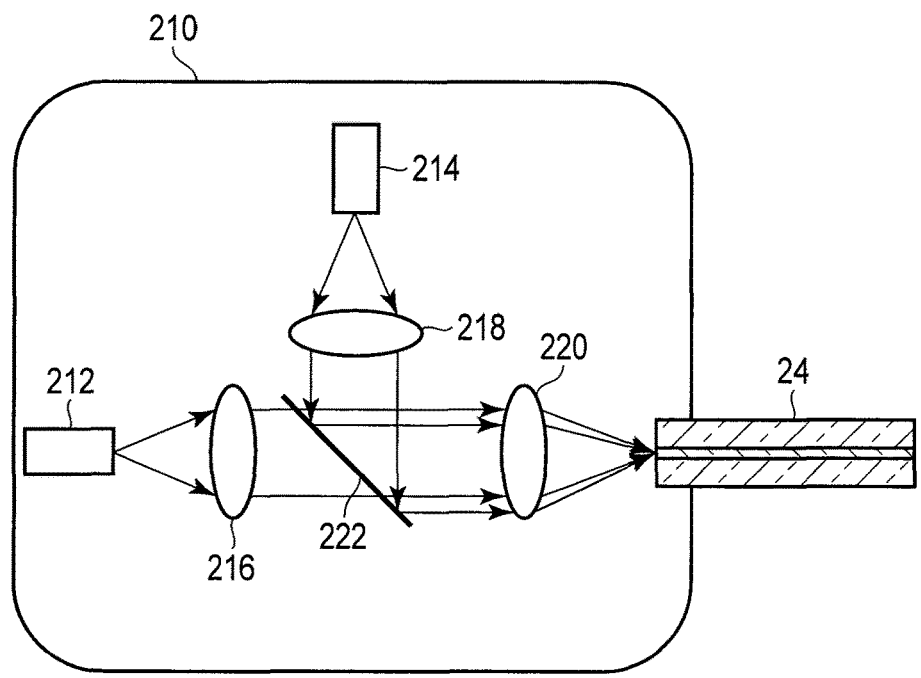
F I G. 12
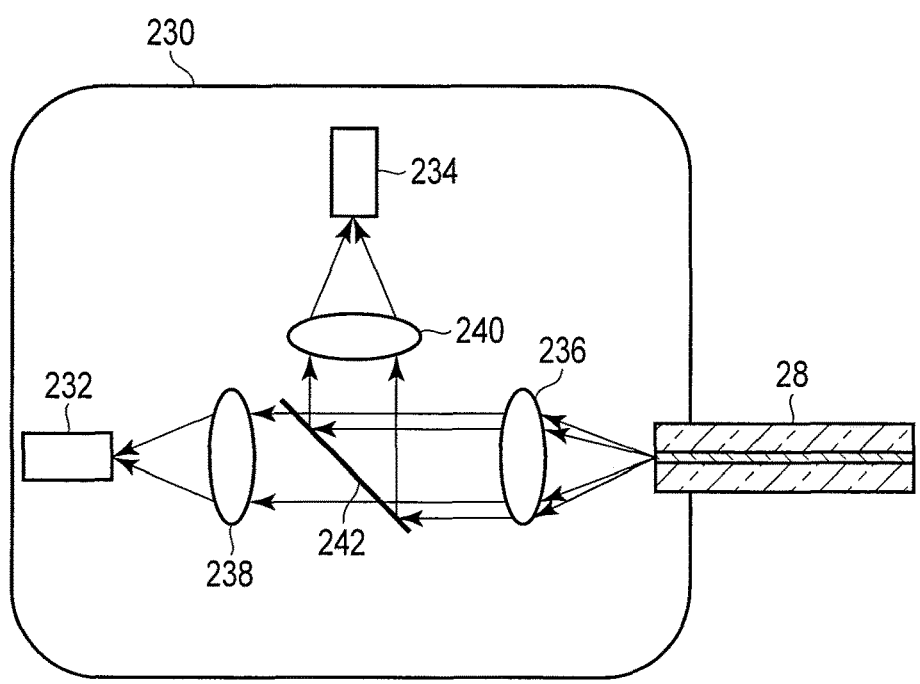
F I G. 13

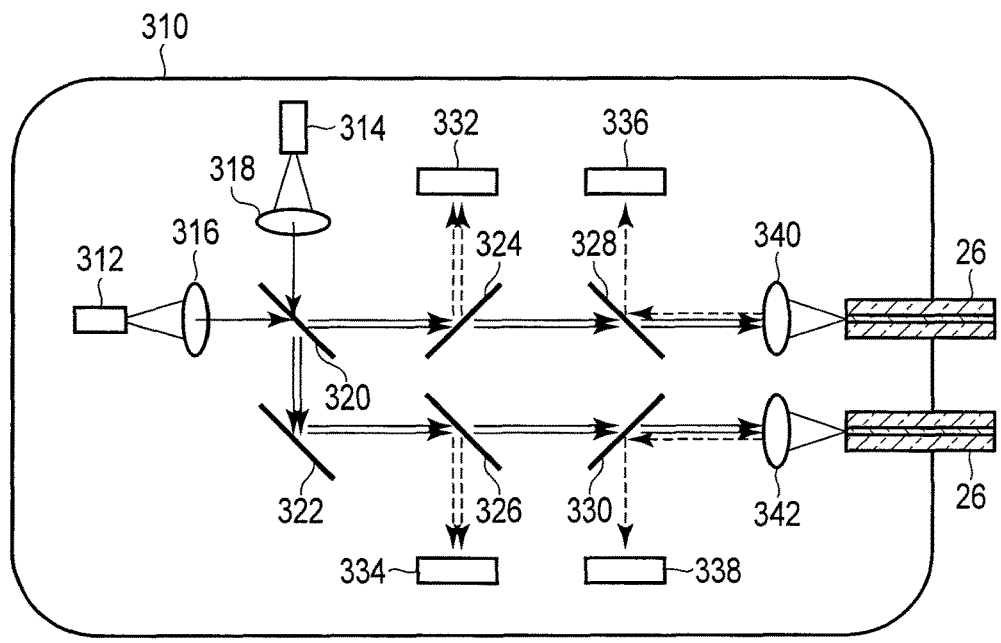
F I G. 18
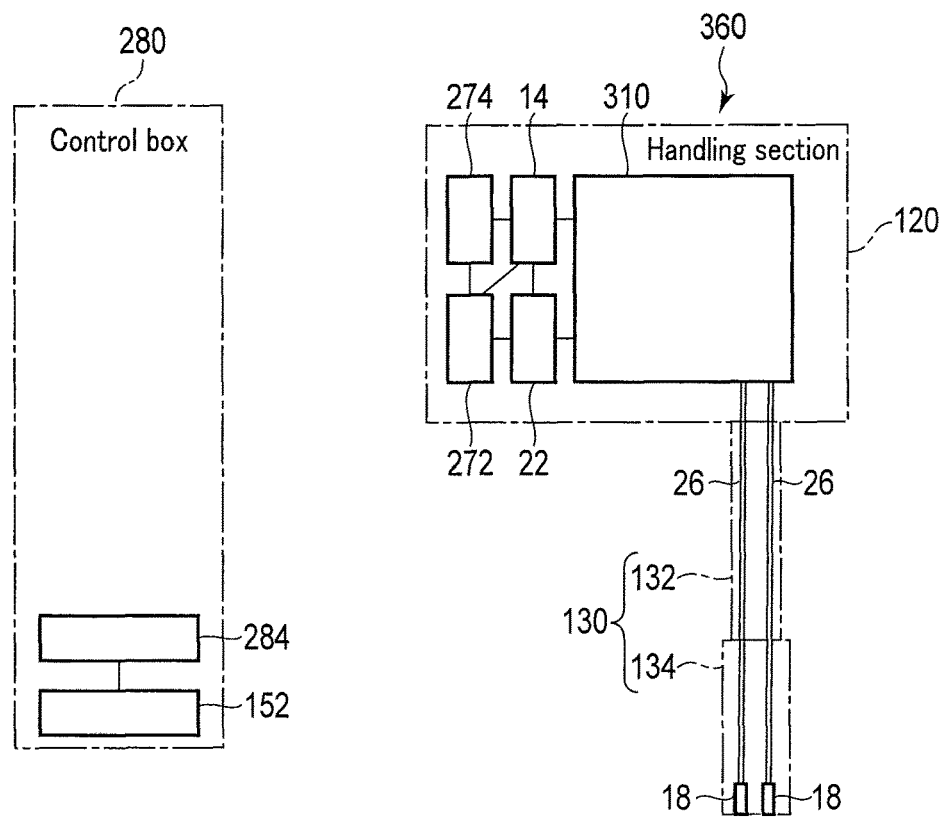
F I G. 19

ENDOSCOPE ILLUMINATION DEVICE

CROSS REFERENCE TO RELATED APPLICATIONS

This application is a continuation application of PCT Application No. PCT/JP2015/078520 filed on Oct. 7, 2015, the entire contents of which are incorporated herein by reference.

BACKGROUND OF THE INVENTION

1. Field of the Invention

The present invention relates to an endoscope illumination device using a single-line light guiding member.

2. Description of the Related Art

As an example of the endoscope illumination device using a single-line light guiding member, an illumination system in which laser light emitted from a laser light source is guided by a single-line optical fiber extending in an endoscope, and wavelength-converted by a fluorescent substance at a distal end section of the endoscope to generate illumination light is disclosed in, for example, Japanese Patent No. 5103874. A safety system achieved by monitoring the light quantity of light that has entered the optical fiber and been wavelength-converted is also presented.

BRIEF SUMMARY OF THE INVENTION

An endoscope illumination device includes a light source that outputs primary light, a light guide that includes a first end face from which the primary light is radiated, and guides the primary light, and a light converter that is disposed to face the first end face, includes a second end face which the primary light enters, converts part of the primary light into secondary light. The illumination device also includes a holder that holds the light guide and the light converter so that an incident angle of the secondary light that is radiated from a point of intersection of the second end face and an optical axis of the light guide on the first end face and enters the first end face is equal to or larger than an acceptance angle (NA) of the light guide.

Additional objects and advantages of the invention will be set forth in the description that follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 5 shows a modification of a distal end unit, which is interchangeable with the distal end unit of FIG. 2.

FIG. 6 shows a modification of a distal end unit, which is interchangeable with the distal end unit of FIG. 2.

FIG. 9 shows a modification of a distal end unit, which is interchangeable with the distal end unit of FIG. 2.

FIG. 10 schematically shows a general configuration of an endoscope apparatus according to the first embodiment.

FIG. 12 shows an LD section according to a second embodiment.

FIG. 13 shows a PD section according to the second embodiment.

FIG. 18 is a detailed view of an LD/PD section according to the third embodiment.

FIG. 19 shows a configuration for mounting the endoscope illumination device of FIG. 17 on the endoscope apparatus of FIG. 15.

DETAILED DESCRIPTION OF THE INVENTION

First Embodiment

A first embodiment will be described with reference to FIGS. 1 to 11.

(Overview of Illumination Device and Safety System)

Figure 1:
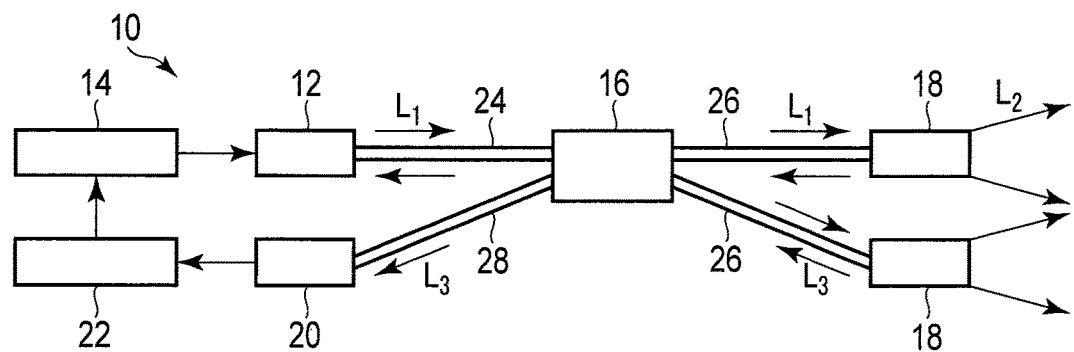
FIG. 1 schematically shows a general configuration of an endoscope illumination device of a first embodiment.

FIG. 1 schematically shows a general configuration of an endoscope illumination device 10 of the present embodiment. Descriptions will be provided following the passage of light.

Laser light $L_1$, which is primary light output from an LD section 12 serving as a light source, is guided by an optical fiber 24 serving as a light guiding member or a light guide, and input to an optical coupler 16 serving as an optical branching member. The optical coupler 16 divides the input laser light $L_1$ in half, and outputs each half to two optical fibers 26, respectively. The laser light $L_1$ guided by the two optical fibers 26 is input to two distal end units 18, respectively.

The distal end units 18 each have a function of converting input laser light $L_1$ into secondary light. Part of the secondary light is radiated from the distal end units 18 as illumination light $L_2$. Part of the secondary light enters the optical fibers 26, and travels opposite in direction to the travel of the primary light as return light $L_3$.

The return light $L_3$ travels through the optical fibers 26 to the optical coupler 16, and is divided by the optical coupler 16 in half. A half travels through the optical fiber 24 to the LD section 12, and the other half travels through an optical fiber 28 to a PD section 20. The return light $L_3$ input to the LD section 12 is applied to an LD element or the periphery of the LD element, and converted into heat. The return light $L_3$ input to the PD section 20 is applied to a PD element serving as a light receiving element, and photoelectrically converted. The PD element outputs a current corresponding to the incident light quantity. The current is measured by a detection circuit 22, and converted into a light value of the return light $L_3$.

The detection circuit 22 further determines whether the measured light value of the return light $L_3$ is normal or abnormal. When the detection circuit 22 determines that the light value is abnormal, it determines that a failure has occurred, and issues to an LD drive circuit 14 an instruction to make the output of the LD section 12 zero or lower than in normal use. The LD drive circuit 14 drives the LD section 12 in accordance with the input instruction. Namely, the detection circuit 22 and the LD drive circuit 14 constitute a control section that controls the LD section 12 based on the light quantity of return light $L_3$.

Always performing such monitoring of return light $L_3$ while driving illumination enables instantaneously detecting a failure and decreasing the output of laser light $L_1$ when a failure occurs in the LD section 12, the optical coupler 16, the distal end units 18, or the optical fibers 24, 26, and 28 connecting sections. This can assure higher safety for users from laser light $L_1$ that is inevitably radiated to the peripheral space due to the failure.

(LD Section 12)

The LD section 12 has a so-called pigtail structure of inserting laser light with a wavelength of 445 nm emitted from an LD element into the optical fiber 24 through a lens.

(Optical Fibers 24, 26, and 28)

A multi-mode optical fiber, which can guide light in multiple modes, is applied to the optical fibers 24, 26, and 28. The multi-mode optical fiber is advantageous over a single-mode optical fiber in that the light insertion efficiency is high because of the large area of the core (light guiding path), and the light quantity of return light $L_3$ can be easily secured as will be described later because of the large NA of the optical fiber. Preferably, the diameter of the core is 50 μm, and the diameter of the clad is 1.2 times the diameter of the core or less, i.e., 60 μm or less. By thinning the clad, the luminous efficiency of the distal end units 18 can be increased as will be described later. The larger the NA, the better. For example, the NA is preferably 0.22 or more. Regarding materials, it is preferable that the core is made of pure quartz, the clad is made of fluorine-doped quartz, and a jacket outside the clad is made of polyimide or ETFE.

(Optical Coupler 16)

The optical coupler 16 is of a so-called 2×2 type including two input ports and two output ports. The optical coupler 16 has a function of combining light input to the two input ports and separating the combined light at a desired branching ratio and outputting light to the two output ports. Here, the branching ratio is fifty-fifty. The optical coupler 16 has a configuration in which, for example, cores of two optical fibers are adjacent to each other, and light is delivered between the adjacent cores. Such an optical coupler 16 may be manufactured by, for example, partly fusion-splicing the two optical fibers, and melting and extending them.

(Distal End Unit 18)

Next, a configuration of the distal end unit 18 will be described with reference to FIG. 2.

The distal end unit 18 includes a fluorescent substance 62 serving as a light converting member or a light converter that converts primary light output from the optical fiber 26 to generate secondary light, and a holder 52 that holds the optical fiber 26 and the fluorescent substance 62.

The optical fiber 26 serving as a light guiding member includes an optical fiber end face 32, which is a light guiding member end face or a light guide end face through which laser light $L_1$, which is primary light, is radiated from the light guiding member. The optical fiber 26 includes a core 34 extending on the central axis of the optical fiber 26, and a clad 36 covering the outer peripheral cylindrical surface of the core 34. The fluorescent substance 62 serving as a light converting member includes a fluorescent substance end face 64, which is a light converting member end face or a light converter end face through which laser light $L_1$, which is primary light, enters the light converting member. The optical fiber 26 and the fluorescent substance 62 are arranged apart from each other in such a manner that the optical fiber end face 32 faces the fluorescent substance end face 64.

(Holder 52)

The holder 52 has a cylindrical outer shape and includes an optical fiber holding hole 54, which is a light guiding member holding hole or a light guide holding hole for holding the optical fiber 26, and a fluorescent substance holding hole 56, which is a light converting member holding hole or a light converter holding hole for holding the fluorescent substance 62. The optical fiber holding hole 54 is a hole having a circular cross section in accordance with the shape of the optical fiber 26, and its hole diameter is larger than the diameter of the optical fiber 26 inserted thereinto. The fluorescent substance holding hole 56 is a hole having a circular cross section like the optical fiber holding hole 54, but has a tapered shape in which the diameter of the hole gradually increases from the optical fiber holding hole 54 side to the illumination light radiating side. The optical fiber holding hole 54 coaxially communicates with the fluorescent substance holding hole 56 within the holder 52, and the diameter of the optical fiber holding hole 54 is coincident with the smallest diameter of the fluorescent substance holding hole 56.

On at least an inner wall of the fluorescent substance holding hole 56, a reflection film 58a with a high reflectivity with respect to both of the primary light and the secondary light emitted from the fluorescent substance 62 is formed. The material of the reflection film 58a is preferably Ag, Al, etc. A protection film 58b for protecting the reflection film 58a may be further formed on the reflection film 58a. The protection film 58b is preferably made of a material having a high transmittance with respect to both of the primary light and the secondary light, such as $SiO_2$ and ITO. These reflection film 58a and protection film 58b may be formed by, for example, plating, sputtering, or an evaporation method.

The optical fiber 26 is bonded and fixed to the holder 52. The optical fiber 26 passes through the optical fiber holding hole 54 of the holder 52, and the optical fiber end face 32 is fixed at a position within the fluorescent substance holding hole 56. An adhesive is not applied to the fluorescent substance holding hole 56, and applied only to the optical fiber holding hole 54 and the outer surface of the holder 52. The optical fiber end face 32 is surface-ground on a plane perpendicular to the optical axis of the optical fiber 26.

(Fluorescent Substance 62)

The fluorescent substance 62 is made of, for example, YAG ceramics. The YAG absorbs part of blue light, and converts it into fluorescent light in the yellow range. Therefore, when laser light with a wavelength of 445 nm is applied to YAG ceramics, part of the laser light is absorbed by the YAG ceramics, converted into yellow fluorescent light, and radiated from the YAG ceramics, whereas part of the laser light passes through the YAG ceramics without being absorbed by the YAG ceramics. As a result, fluorescent light having yellow components is added to laser light originally having blue components, whereby white illumination light can be obtained. For such a way of making white light, ceramic materials are not necessarily used. For example, the case where a monocrystal of YAG is used, and the case where a bound body obtained by glass- or resin-sealing YAG powders is used are conceivable and, in either case, white light can be generated in the same way.

In addition, the fluorescent substance 62 is columnar, and provided within the fluorescent substance holding hole 56 of the holder 52. The fluorescent substance 62 has such a diameter so as to provide the fluorescent substance 62 with an area allowing all laser light $L_4$ radiated from the optical fiber end face 32 of the optical fiber 26 to be applied to the fluorescent substance 62.

In the fluorescent substance holding hole 56 of the holder 52, a transparent member 72 is provided closer to the optical fiber 26 than the fluorescent substance end face 64. This transparent member 72 controls the interval between the optical fiber end face 32 and the fluorescent substance end face 64 on the optical axis of the optical fiber 26, i.e., the distance therebetween. Namely, the transparent member 72 functions as an interval keeping member that defines the distance between the optical fiber end face 32 and the fluorescent substance end face 64. In the remaining portion of the fluorescent substance holding hole 56 of the holder 52, a transparent member 74 is provided. The transparent members 72 and 74 are made of a material, such as a silicon resin, having a high lightfastness and a high transmittance with respect to the primary light and the secondary light. As the material of the transparent members 72 and 74, an epoxy resin, glass, and the like may be used as well as the silicon resin. In addition, the transparent members 72 and 74 may be made of different materials. For example, the transparent members 72 and 74 may be made of glass and a silicon resin, respectively.

The transparent members 72 and 74 are not essential, and one or both of them may be omitted as the case may be. When the transparent member 74 is omitted, the transparent member 72 functions as the interval keeping member, as described above. When the transparent member 72 is omitted, or when the transparent members 72 and 74 are omitted, the interval between the optical fiber end face 32 and the fluorescent substance end face 64 on the optical axis of the optical fiber 26 is controlled by the holder 52. Namely, in this case, the holder 52 functions as an interval keeping member that defines the distance between the optical fiber end face 32 and the fluorescent substance end face 64.

Here, the distance L between the optical fiber end face 32 and the fluorescent substance end face 64 on the optical axis of the optical fiber 26 is described. Properly setting the distance L is important in inserting as much fluorescent light as possible into the optical fiber 26 from the distal end unit 18. The primary light applied from the optical fiber 26 to the fluorescent substance 62 passes through the transparent member 72, enters the fluorescent substance end face 64, and is converted into fluorescent light. At this time, the intensity distribution of the primary light in a direction perpendicular to the optical axis of the optical fiber 26 is a Gaussian distribution in which the middle part is very high. Namely, most components of the primary light are converted into fluorescent light within the fluorescent substance 62 near the intersection of the optical axis of the optical fiber 26 and the fluorescent substance end face 64. Therefore, that point within the fluorescent substance 62 can be considered as a luminous point 66 of fluorescent light. The fluorescent light obtained by conversion at the fluorescent substance 62 and radiated therefrom has a uniform distribution in all directions, and the quantity of fluorescent light that enters the optical fiber end face 32 can be approximately evaluated by a solid angle of the optical fiber end face 32 from the luminous point 66. This solid angle is largest when the optical fiber end face 32 is coincident with the fluorescent substance end face 64, i.e., when the optical fiber 26 is in contact with the fluorescent substance 62 on the optical axis of the optical fiber 26, as a matter of course.

However, it is very difficult to bring the optical fiber 26 in contact with the fluorescent substance 62 on the optical axis with no gap therebetween. When surfaces are in contact with each other, the center parts of the surfaces are hardly in contact. In many cases, an edge portion of the end face of the optical fiber 26 comes into contact with the fluorescent substance 62, and a gap appears in the center. Bringing the optical fiber 26 into contact with the fluorescent substance 62 is also disadvantageous in manufacturing. The optical fiber 26 is a quartz rod of several ten to several hundred µm, and very easily chips or cracks. Bringing the optical fiber 26 into contact with the fluorescent substance 62 may significantly decrease the yield ratio in manufacturing. For such a reason, the optical fiber 26 and the fluorescent substance 62 are arranged apart from each other in general.

Meanwhile, all components of the fluorescent light that has entered the optical fiber end face 32 do not travel reversely in the optical fiber 26 as return light $L_3$. The optical fiber 26 has an NA (acceptance angle) determined based on the refractive index difference between the core 34 and the clad 36. Namely, even if light enters the optical fiber 26, when the incident angle is equal to or larger than the NA accepted by the optical fiber 26, light cannot be confined by the clad 36, and immediately travels out of the optical fiber 26. Accordingly, even if the optical fiber 26 is brought closest to the fluorescent substance 62 to allow more fluorescent light to enter the optical fiber end face 32, it will only increase light with an incident angle that cannot be guided by the optical fiber 26, and does not increase the light quantity of return light $L_3$ that reaches the PD section 20.

Figure 3:
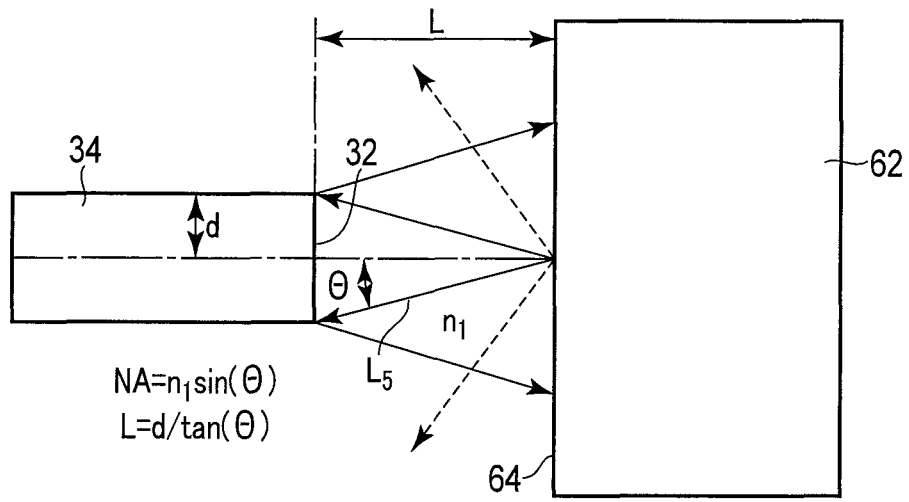
FIG. 3 illustrates equations of a distance between an optical fiber and fluorescent substance shown in FIG. 2.

In consideration of the above, an appropriate range of the distance L between the optical fiber end face 32 and the fluorescent substance end face 64 on the optical axis of the optical fiber 26 can be set. The condition for making the light quantity of the return light $L_3$ largest is that, with the optical fiber 26 and the fluorescent substance 62 always arranged apart from each other, the solid angle of the optical fiber end face 32 from the point of intersection of the optical axis of the optical fiber 26 and the fluorescent substance end face 64 is equal to or larger than the acceptance NA of the optical fiber 26. Where the radius of the core 34 of the optical fiber 26 is d, the acceptable angle of the optical fiber 26 is NA, the refractive index of the transparent member 72 is n, the incident angle of fluorescent light $L_5$ that is emitted from the point of intersection of the optical axis of the optical fiber 26 and the fluorescent substance end face 64 and enters the periphery of the core 34 of the optical fiber 26 is Θ as shown in FIG. 3, the following relational equations can be obtained:

$NA = n_1 \sin(\Theta)$ $L \leq d/\tan(\Theta)$

By canceling Θ from those two equations to obtain L, and regarding the obtained L as a critical value, the following relational equation can be obtained:

$$L \leq \frac{d \times n \times \sqrt{1 - \left(\frac{NA}{n}\right)^2}}{NA}$$

In the present embodiment, the distance L between the optical fiber end face 32 and the fluorescent substance end face 64 on the optical axis of the optical fiber 26 is set to satisfy this relationship.

As a result, the light quantity of return light $L_3$ that enters the optical fiber 26 and is guided by the optical fiber 26 is improved. Consequently, a sufficient light quantity can be assured even for detection by a low-priced light receiving element having low sensitivity, and a safety system that stably operates even with a low-priced light receiving element can be constructed.

(Modification of Distal End Unit 18)

Figure 2:
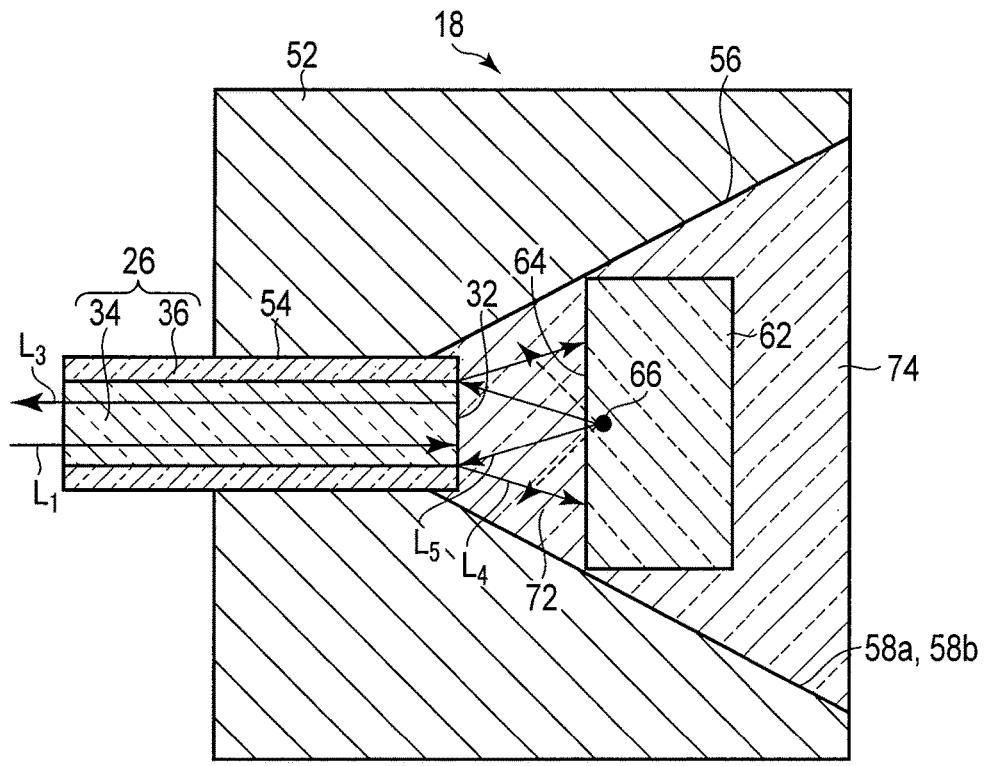
FIG. 2 is a cross-sectional view showing details of a distal end unit shown in FIG. 1.

FIGS. 4-9 show modifications of the distal end unit 18, which are interchangeable with the distal end unit 18 of FIG. 2. These modified distal end units 18 are intended to further improve the light quantity of return light $L_3$.

The distal end units 18 shown in FIGS. 4-7 are intended to further improve the light quantity of return light $L_3$ by providing a lens function to the interface between the optical fiber 26 and the transparent member 72, which is coincident with the optical fiber end face 32, and the interface between the fluorescent substance 62 and the transparent member 72, which is coincident with the fluorescent substance end face 64.

Figure 4:
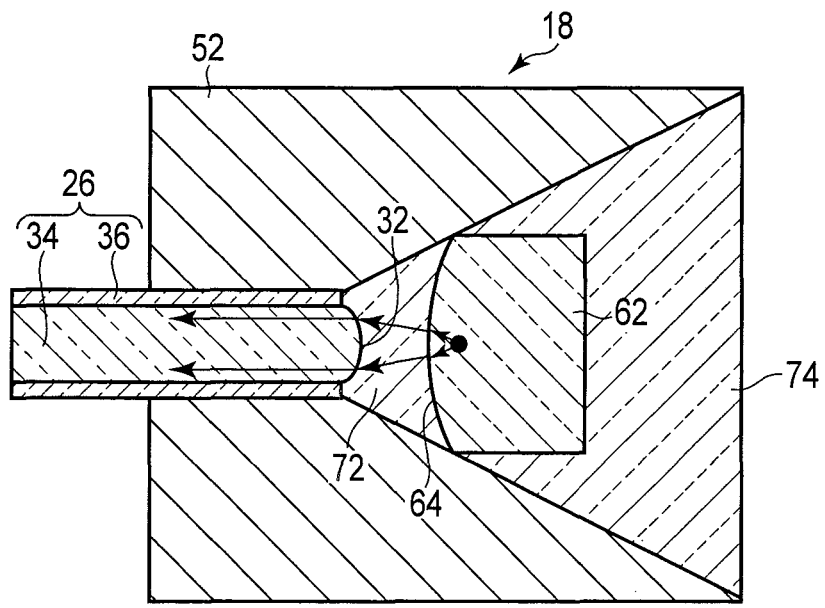
FIG. 4 shows a modification of the distal end unit, which is interchangeable with the distal end unit of FIG. 2.

In the distal end unit 18 shown in FIG. 4, the optical fiber end face 32 is convex, and the fluorescent substance end face 64 is convex. In addition, the refractive indexes of the core 34 of the optical fiber 26, the transparent member 72, and the fluorescent substance 62 satisfy the relationships (refractive index of the core 34 of the optical fiber 26)>(refractive index of the transparent member 72) and (refractive index of the fluorescent substance 62)>(refractive index of the transparent member 72). Accordingly, the interface between the fluorescent substance 62 and the transparent member 72 and that between the core 34 of the optical fiber 26 and the transparent member 72 both converge return light. Specifically, the interface between the fluorescent substance 62 and the transparent member 72 acts on the return light from within the fluorescent substance 62 to reduce the divergence angle with respect to the optical axis. The interface between the transparent member 72 and the core 34 of the optical fiber 26 also acts on the return light from the transparent member 72 to reduce the divergence angle with respect to the optical axis. Therefore, both interfaces contribute to increase in the light quantity of return light $L_3$ in comparison with the case where they are plane.

In the distal end unit 18 shown in FIG. 5, the optical fiber end face 32 is convex, and the fluorescent substance end face 64 is concave. In addition, the refractive indexes of the core 34 of the optical fiber 26, the transparent member 72, and the fluorescent substance 62 satisfy the relationship (refractive index of the core 34 of the optical fiber 26)>(refractive index of the transparent member 72)>(refractive index of the fluorescent substance 62). Accordingly, the interface between the fluorescent substance 62 and the transparent member 72 acts on the return light from within the fluorescent substance 62 to reduce the divergence angle with respect to the optical axis. The interface between the transparent member 72 and the core 34 of the optical fiber 26 also acts on the return light from the transparent member 72 to reduce the divergence angle with respect to the optical axis. Therefore, both interfaces contribute to increase in the light quantity of return light $L_3$ in comparison with the case where they are plane.

In the distal end unit 18 shown in FIG. 6, the optical fiber end face 32 is concave, and the fluorescent substance end face 64 is concave. In addition, the refractive indexes of the core 34 of the optical fiber 26, the transparent member 72, and the fluorescent substance 62 satisfy the relationships (refractive index of the core 34 of the optical fiber 26)< (refractive index of the transparent member 72) and (refractive index of the fluorescent substance 62)<(refractive index of the transparent member 72). Accordingly, the interface between the fluorescent substance 62 and the transparent member 72 acts on the return light from within the fluorescent substance 62 to reduce the divergence angle with respect to the optical axis. The interface between the transparent member 72 and the core 34 of the optical fiber 26 also acts on the return light from the transparent member 72 to reduce the divergence angle with respect to the optical axis. Therefore, both interfaces contribute to increase in the light quantity of return light $L_3$ in comparison with the case where they are plane.

Figure 7:
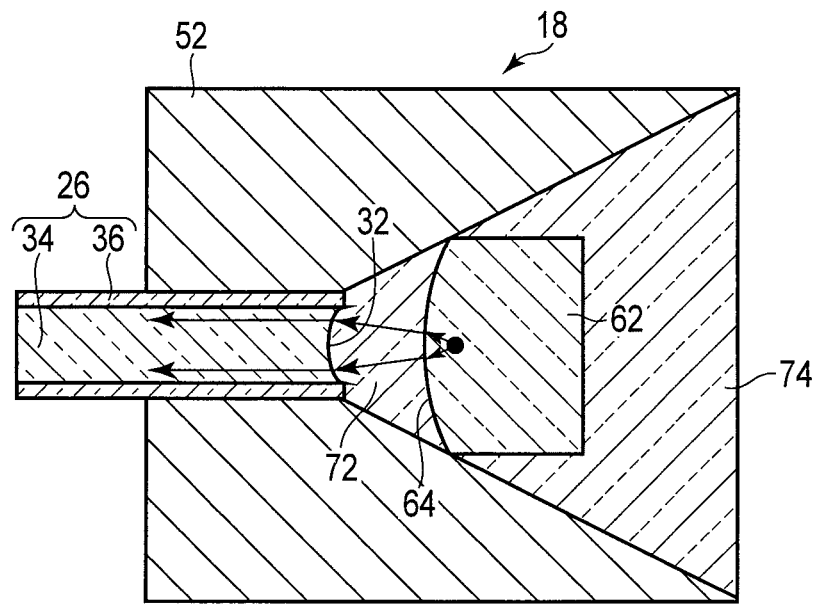
FIG. 7 shows a modification of a distal end unit, which is interchangeable with the distal end unit of FIG. 2.

In the distal end unit 18 shown in FIG. 7, the optical fiber end face 32 is concave, and the fluorescent substance end face 64 is convex. In addition, the refractive indexes of the core 34 of the optical fiber 26, the transparent member 72, and the fluorescent substance 62 satisfy the relationship (refractive index of the core 34 of the optical fiber 26)< (refractive index of the transparent member 72)<(refractive index of the fluorescent substance 62). Accordingly, the interface between the fluorescent substance 62 and the transparent member 72 acts on the return light from inside the fluorescent substance 62 to reduce the divergence angle with respect to the optical axis. The interface between the transparent member 72 and the core 34 of the optical fiber 26 also acts on the return light from the transparent member 72 to reduce the divergence angle with respect to the optical axis. Therefore, both interfaces contribute to increase in the light quantity of return light $L_3$ in comparison with the case where they are plane.

In the distal end units 18 shown in FIGS. 4-7, both of the interface between the fluorescent substance 62 and the transparent member 72 and that between the transparent member 72 and the optical fiber 26 have a lens function; however, one of the two interfaces may have the lens function, and the effect of increasing the light quantity of return light $L_3$ can also be produced with such a configuration. The end face of the clad 36 may be concave or convex to be continuous with the core 34 in correspondence with the convex or concave surface of the core 34, or may be a plane surface.

Figure 8:
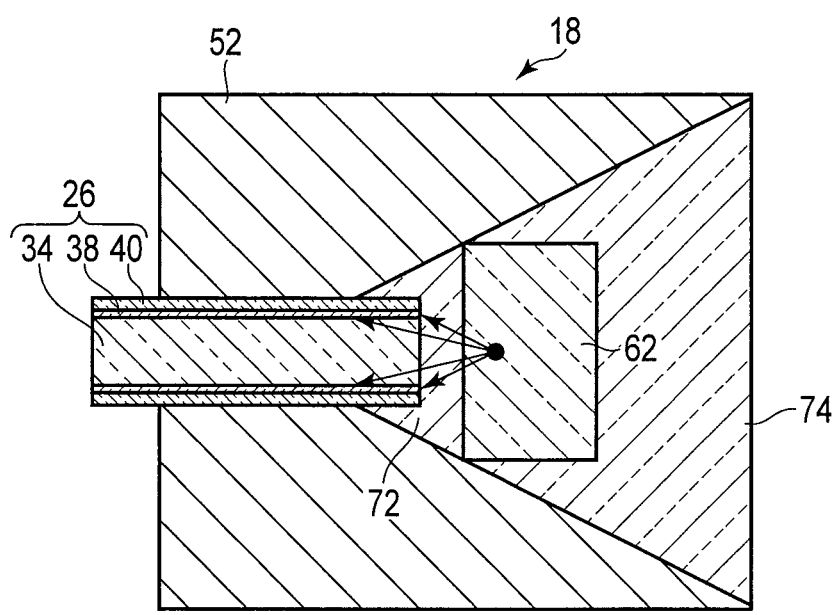
FIG. 8 shows a modification of a distal end unit, which is interchangeable with the distal end unit of FIG. 2.

In the distal end unit 18 shown in FIG. 8, the optical fiber 26 is a double-clad optical fiber, and includes a core 34 extending its central axis, a primary clad 38 covering the outer peripheral cylindrical surface of the core 34, and a secondary clad 40 covering the outer peripheral cylindrical surface of the primary clad 38. Optical fiber 26 having such a double-clad structure not only guides return light that has entered the core 34 by the confining effect of the primary clad 38, but also guides return light that has entered the primary clad 38 by the confining effect of the secondary clad 40. Namely, the optical fiber 26 including two clads has a larger acceptance angle than an optical fiber including only one clad. Accordingly, the light quantity of return light $L_3$ can be increased.

In the distal end unit 18 shown in FIG. 9, the optical fiber 26 includes a core 34 extending its central axis, a clad 36 covering the outer peripheral cylindrical surface of the core 34, and a metal reflection film 42 covering the outer peripheral cylindrical surface of the clad 36. The metal reflection film 42 produces an effect of confining, in the optical fiber 26, components that have entered the optical fiber 26, but have an incident angle exceeding the NA of the optical fiber 26. Accordingly, the light quantity of return light $L_3$ can be further increased.

(Failure Determination)

For failure determination, various methods are conceivable; however, only one example will be described. For example, the detection circuit 22 records the light value of return light $L_3$ at a normal time with respect to an LD output value or LD injection current in a normal-time table. When return light $L_3$ is monitored, the LD injection current to the LD section 12 and the light value of return light $L_3$ from the PD section 20 are compared with those in the normal-time table and, for example, when the measured light value of return light $L_3$ with respect to an LD injection current becomes the threshold of 50% or less of the light value of return light $L_3$ at the normal time, it is determined that a failure has occurred. When a minor failure should also be detected, it is desirable to set the threshold to a high percentage, such as 90%. However, if the threshold is too high, a malfunction may occur due to variations of return light $L_3$ at the normal time. Therefore, it is desirable to set the threshold to a highest possible percentage within the bounds of not causing a malfunction in a normal use environment.

(Configuration for Mounting in Endoscope)

Figure 11:
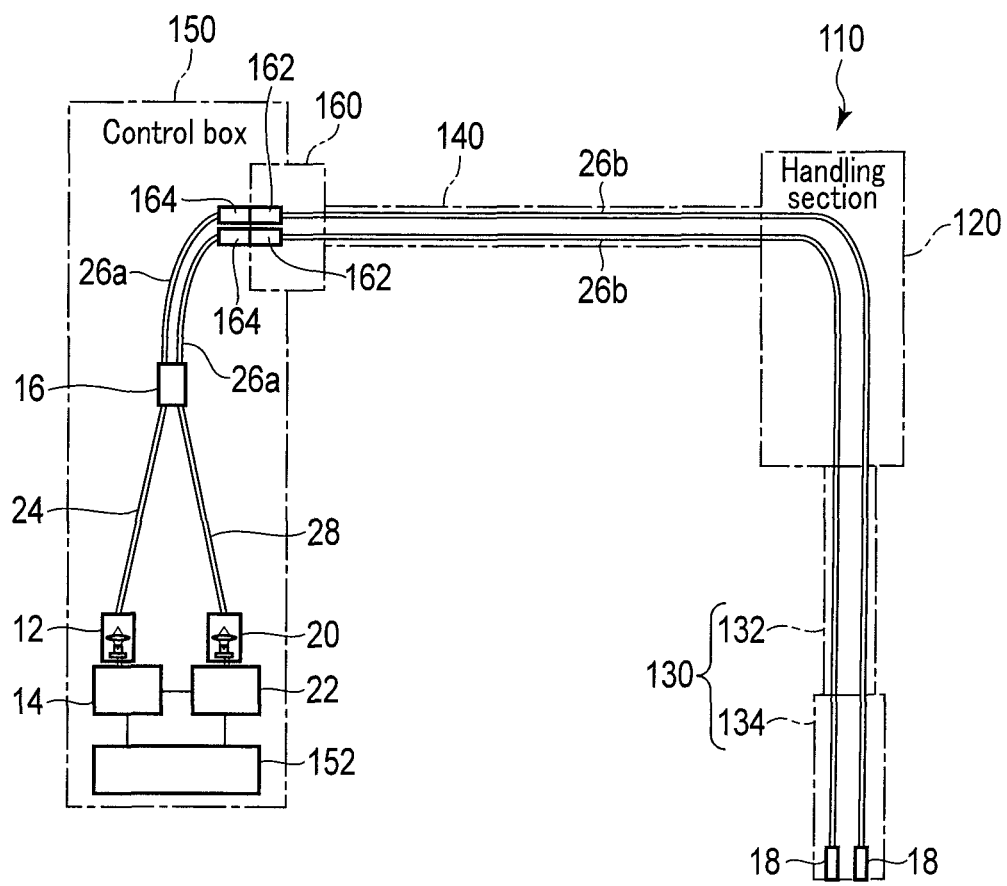
FIG. 11 shows a configuration for mounting the endoscope illumination device of FIG. 1 on the endoscope apparatus of FIG. 10.

A configuration for mounting the endoscope illumination device of the present embodiment in an endoscope will be described. FIG. 10 schematically shows a general configuration of the endoscope apparatus according to the embodiment, and FIG. 11 shows a configuration for mounting the endoscope illumination device of FIG. 1 in the endoscope apparatus of FIG. 10.

An endoscope 110 includes a handling section 120 and a thin insertion section 130 extending from the handling section 120. The insertion section 130 includes an insertion cable 132, part of which is flexible, and a hard distal end section 134. A connection cable 140 extends from the handling section 130. The connection cable 140 is a tube partly having flexibility, but maintaining necessary rigidity. The connection cable 140 is connected by an optical connector 160 to a control box 150 having a rigid housing.

The control box 150 contains therein the LD section 12 serving as a light source, the LD drive circuit 14 that controls the LD section 12, the optical coupler 16 serving as an optical branching member, the optical fiber 24 that connects the LD section 12 to the optical coupler 16, the PD section 20 serving as a light detector, the optical fiber 28 that connects the optical coupler 16 to the PD section 20, and the detection circuit 22. The LD drive circuit 14 and the detection circuit 22 are electrically connected to a system control substrate 152 on which a system control section that controls the entire endoscope system, such as imaging, is mounted.

Two optical fibers 26a extend from the optical coupler 16 and are terminated at a control box side optical connector 164 of the optical connector 160. An endoscope side optical connector 162 of the optical connector 160 is connected to two optical fibers 26b. The optical fibers 26a are optically connected to the optical fibers 26b through the optical connector 160. The optical fibers 26b extend to the distal end section 134 of the insertion section 130 through the insides of the connection cable 140, the handling section 120, and the insertion cable 132 of the insertion section 130, and are connected to the distal end units 18 provided in the distal end section 134 of the insertion section 130. The optical fibers 26a and optical fibers 26b correspond to the optical fibers 26 shown in FIG. 1.

In the LD section 12, laser light $L_1$ output from an LD element is converged by a converging lens and enters the optical fiber 24. The laser light $L_1$ is guided by the optical fiber 24 and input to the optical coupler 16. The optical coupler 16 splits the input laser light $L_1$ in half and outputs each half to the two optical fibers 26a, respectively. The laser light $L_1$ is guided by the optical fibers 26a and input to the optical fibers 26b through the optical connector 160. The laser light $L_1$ is guided by the optical fibers 26a extending through the insides of the connection cable 140, the handling section 120, and the insertion section 130, and enters the two distal end units 18. Part of the laser light $L_1$ that has entered the distal end units 18 is converted into fluorescent light by the fluorescent substance 62. Part of the fluorescent light is radiated from the distal end section 134 to the outside as illumination light $L_2$.

Part of the fluorescent light, into which the laser light $L_1$ is converted, enters the optical fibers 26b and travels reversely in the paths of laser light $L_1$ as return light $L_3$. Return light $L_3$ that has reached the optical coupler 16 is split in half by the optical coupler 16 for the LD section 12 and the PD section 20. The return light $L_3$ that has reached the PD section 20 is detected by the PD element in the PD section 20. The detection circuit 22 or the system control section on the system control substrate 152 determines whether a failure occurs based on the detection result obtained by the PD section 20 and sends a drive signal corresponding to the determination result to the LD drive circuit 14.

(Other Modifications)

The present embodiment proposes an illumination system using a fluorescent substance 62 as a light converting member; however, a similar safety system can be constructed by other methods. For example, a configuration of mounting an RGB LD element in the LD section 12 and mounting a diffusion member as a light converting member is conceivable. Using RGB or further multi-light laser light by combining the light in the LD section 12 can achieve a higher color-rendering white color and various types of special light. On the other hand, the distal end unit 18 does not need to perform wavelength conversion, but includes, for example, a diffusion member that converts input laser light to have a desired light distribution. The diffusion member is formed by mixing a transparent binder such as a silicon resin with alumina particles having a different refractive index from the silicon resin to cure the silicon resin. Regarding the return light, where the direction from the optical fiber to the diffusion member is forward, and the direction from the diffusion member to the optical fiber is backward, the backward scattering light from the diffusion member is used as return light, as in the case of the fluorescent substance 62. Different from the case of fluorescent light uniformly radiated in all directions, light is intensely radiated forward and backward in the case of diffusion phenomena; therefore, the forward scattering light and the backward scattering light can be efficiently used as illumination light and return light, respectively.

Second Embodiment

Next, a second embodiment will be described with reference to FIGS. 12 to 16. In these figures, the same members as those shown in FIGS. 1 to 11 are assigned the same reference numerals as those shown in FIGS. 1 to 11, and detailed descriptions thereof are omitted. Hereinafter, only points different from the first embodiment will be described. Namely, the parts not described below are the same as those in the first embodiment.

(LD Section 210)

FIG. 12 shows a configuration of an LD section 210 in the second embodiment. The LD section 210 includes an LD element 212 that emits laser light with a wavelength of 445 nm, an LD element 214 that emits laser light with a wavelength of 405 nm, a collimate lens 216 that collimates a beam of the laser light from the LD element 212, a collimate lens 218 that collimates a beam of the laser light from the LD element 214, and a dichroic mirror 222 that combines the laser light from the LD element 212 with the laser light from the LD element 214. The dichroic mirror is designed to transmit light with a wavelength of 445 nm and reflect light with a wavelength of 405 nm. The LD section 210 further includes a lens 220 that causes laser light combined by the dichroic mirror 222 to enter the optical fiber 24. With this configuration, laser light with two wavelengths of 405 nm and 445 nm can be output from the LD section 210.

(PD Section 230)

FIG. 13 shows a configuration of a PD section 230 in the second embodiment. The PD section 230 differs from that in the first embodiment in terms of wavelength-separating return light and measuring the light quantity in two wavelength ranges. Specifically, the two wavelength ranges are a fluorescent light wavelength range from 470 to 750 nm, and an excitation light wavelength range from 400 to 470 nm. The PD section 230 includes a collimate lens 236 that collimates a beam of return light radiated from the optical fiber 28 and a dichroic mirror 242 that splits light from the collimate lens 236. The dichroic mirror 242 is designed to transmit light in a wavelength range from 470 to 750 nm and reflect light in a wavelength range from 400 to 470 nm. The PD section 230 further includes a PD element 232 for detecting light transmitted through the dichroic mirror 242, a PD element 234 for detecting light reflected by the dichroic mirror 242, a lens 238 that converges a beam of light transmitted through the dichroic mirror 242 into PD element 232 and a lens 240 that converges a beam of light reflected by the dichroic mirror 242 into PD element 234. With this configuration, the light quantities of return light in the above two wavelength ranges can be measured at two PD elements 232 and 234, respectively.

(Distal End Unit 250)

Figure 14:
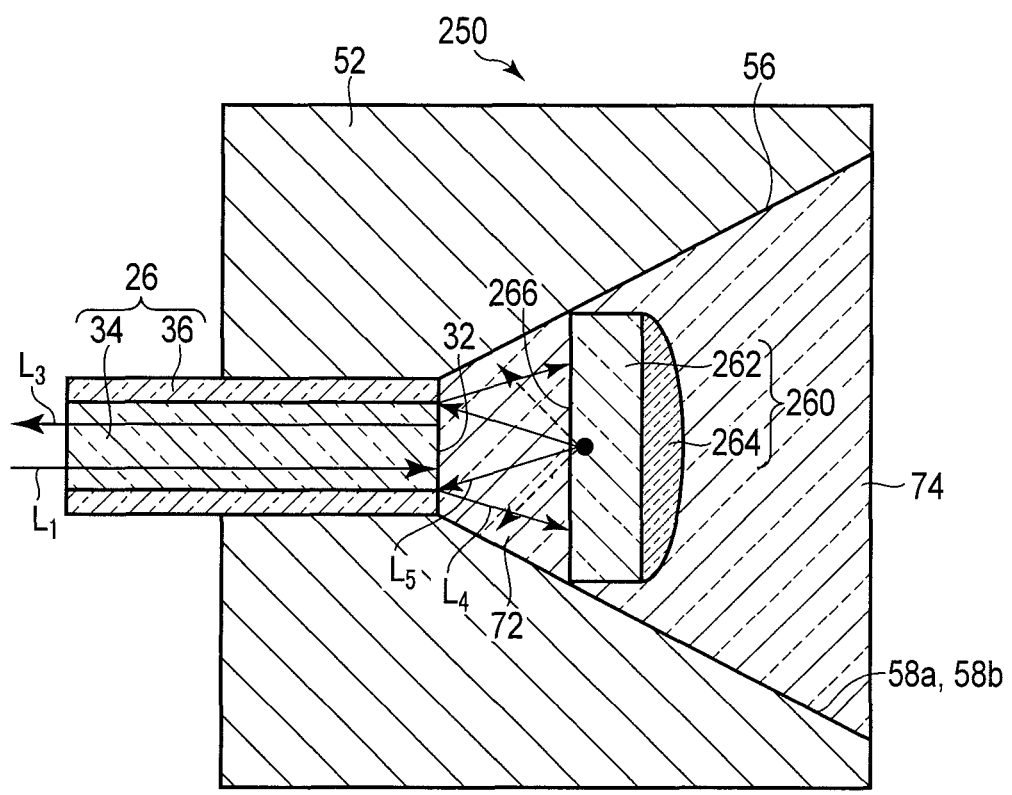
FIG. 14 shows a distal end unit according to the second embodiment.

FIG. 14 shows a configuration of a distal end unit 250 in the second embodiment. The configuration of the fluorescent substance 260 differs from that in the first embodiment. In the present embodiment, two types of fluorescent substances are stacked along an optical axis. In the fluorescent substance 260, for example, a green fluorescent substance 264 is stacked on a yellow fluorescent substance 262. The yellow fluorescent substance 262 may be made of, for example, YAG ceramics, like the fluorescent substance 62 in the first embodiment. The green fluorescent substance 264 is formed in a dome shape on a surface facing a fluorescent substance end face 266 of the yellow fluorescent substance 262. This green fluorescent substance 264 is formed by mixing a transparent resin having a high transmittance with respect to primary light and fluorescent light with green fluorescent substance particles that absorb light with a wavelength of 405 nm and wavelength-convert it into light in the green wavelength range and diffusion particles having a different refraction index from the transparent resin. Specifically, a silicon resin, an epoxy resin, or the like is selected as the transparent resin. It is preferable to provide a gap between the refraction indexes of the diffusion particles and the transparent resin, which causes a diffusion phenomenon when primary light strikes diffusion particles. Therefore, the diffusion particles are made of alumina, titanium oxide, or the like, and have a particle diameter of the order of several μm. A specific production method will be described. A mixture of an uncured transparent resin and diffusion particles is applied to the yellow fluorescent substance 262. The applied transparent resin forms a dome shape by its own surface tension. By controlling the application quantity, a dome shape with an intended curvature may be formed. After that, a green fluorescent substance 264 is formed by curing the transparent resin. In the present embodiment, the central angle of the dome shape is preferably 180 degrees or less to prevent the transparent resin from flowing from the yellow fluorescent substance 262 to the side. The quantity of conversion into green fluorescent light and the degree of diffusion may be adjusted by changing the concentrations of the green fluorescent light particles and diffusion particles mixed in the transparent resin.

The yellow fluorescent substance 262 and the green fluorescent substance 264 are used as follows. First, when laser light with a wavelength of 445 nm is input to the distal end unit 250, the yellow fluorescent substance 262 absorbs part of blue laser light and emits yellow fluorescent light. White illumination light can be obtained by blue laser light and yellow fluorescent light. The diffusion particles within the green fluorescent substance 264 diffuse blue laser light and yellow fluorescent light and contribute to acquirement of a desired light distribution angle. Next, when laser light with a wavelength of 405 nm is input to the distal end unit 250, blue-violet laser light is not absorbed by and is transmitted through the yellow fluorescent substance 262, and is input to the green fluorescent substance 264. The green fluorescent substance 264 absorbs part of the blue-violet laser light and emits green fluorescent light. By using the blue-violet laser light and green fluorescent light transmitted through the yellow fluorescent substance 262 as observation light, application of special light for obtaining an enhanced image of, for example, blood vessels is possible. The diffusion particles work in the same manner as in the case of white illumination. The concentration of the diffusion particles is adjusted in accordance with a desired light distribution angle.

(Failure Determination)

The PD section 230 of the present embodiment can separately measure return light in two wavelength ranges. As described above, by performing separate measurement in the excitation light wavelength range including light of wavelengths of 405 nm and 445 nm and a fluorescent light wavelength range including yellow fluorescent light and green fluorescent light, possible failure modes can be further narrowed down. In the distal end unit 250, there is not only return light of fluorescent light, but also return light of excitation light that enters the optical fiber 26 after repeated diffusion/scattering in the holder 52. Therefore, the return light that returns to the PD section 230 actually includes excitation light and fluorescent light. In addition to monitoring of the light quantity of return light of fluorescent light with respect to an LD injection current as described in the first embodiment, measurement of the light quantity of return light of excitation light is possible. Therefore, the ratios of excitation light components and fluorescent light components to the whole light quantity of return light can also be monitored. For example, when a failure occurs in the fluorescent substance 260, the excitation light components do not change much and the light quantity of return light of fluorescent light decreases. In contrast, when no failure occurs in the distal end unit 250 and a failure occurs in an LD element or the optical coupler 16, the quantity of excitation light input to the distal end unit 250 decreases, which results in a decrease in the light quantity of return light of fluorescent light, as well as a decrease in the light quantity of return light of excitation light. In either case, monitoring of only fluorescent light enables detection of the presence/absence of a failure, but cannot identify a failure part. However, when the light quantities of return light of fluorescent light and excitation light are monitored, a failure part can also be identified. Identification of a failure part enables distinction between a failure that instantly poses a danger to a user, such as a drop of a fluorescent substance, which causes direct application of laser light to the user, and a failure that does not pose a danger to a user for a certain period of time, such as a failure that causes laser light irradiation within an endoscope.

This produces a difference in how to deal with the failure. In the case of the failure that instantly poses a danger to a user, such as a drop of a fluorescent substance, LD driving is instantly stopped; otherwise, low-power driving is required. However, in the case of the failure that does not pose a danger to a user for a certain period of time, lighting only one light even for a short time can avoid a risk of further damaging a lumen or a scope by pulling the scope from the lumen in a dark condition, for example.

As a modification, the wavelength range detected at the PD section 230 may be two wavelength ranges of yellow fluorescent light and green fluorescent light. For example, in the case of simultaneous application of white illumination and special light illumination, a failure of the yellow fluorescent substance 262 and that of the green fluorescent substance 264 can be separately determined. In this case, regarding the positional relationship between the optical fiber 26 and the fluorescent substance 260 described in the first embodiment, the laser incident end face of the yellow fluorescent substance 262 and that of the green fluorescent substance 264 should satisfy the same positional relationship.

(Configuration for Mounting in Endoscope)

Figure 15:
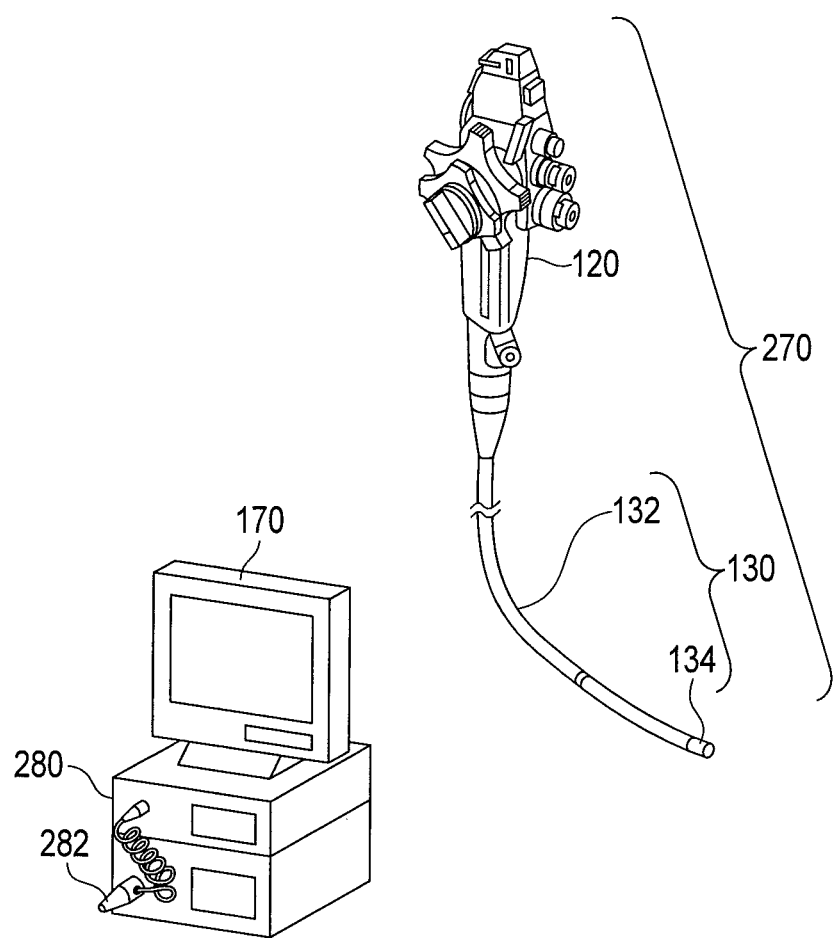
FIG. 15 schematically shows a general configuration of an endoscope apparatus according to the second embodiment.
Figure 16:
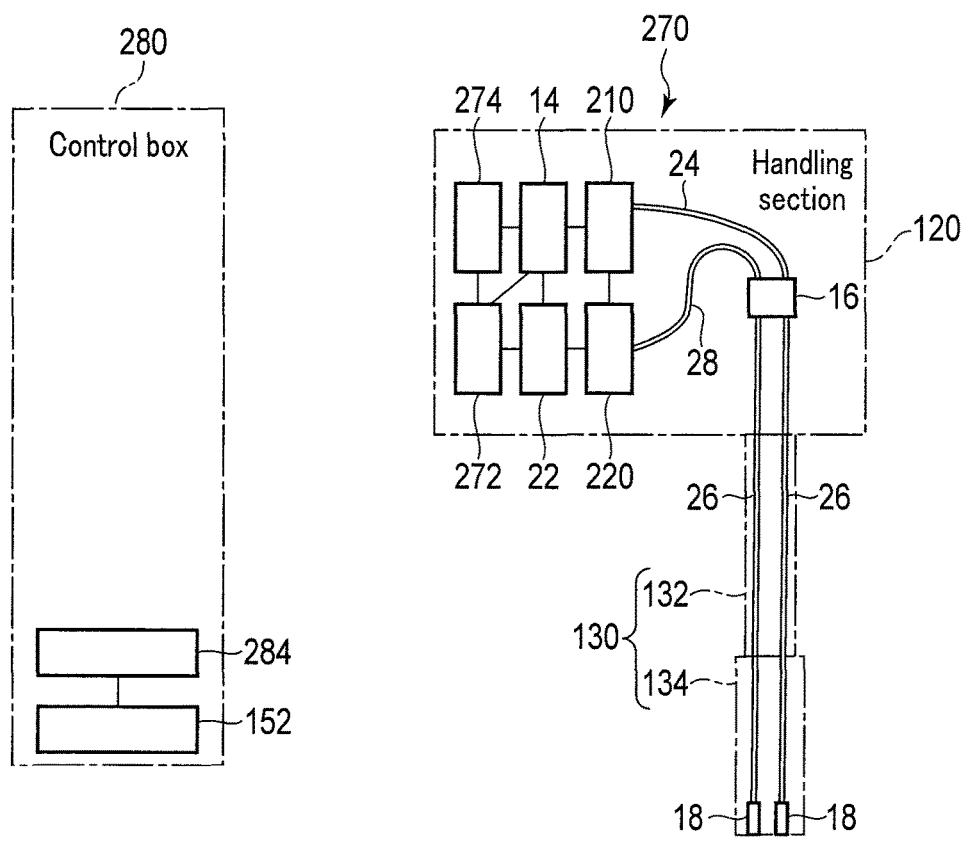
FIG. 16 shows a configuration for mounting an endoscope illumination device of the second embodiment on the endoscope apparatus of FIG. 15.

A configuration for mounting the endoscope illumination device of the present embodiment in an endoscope will be described. FIG. 15 schematically shows a general configuration of the endoscope apparatus according to the second embodiment, and FIG. 16 shows a configuration for mounting the endoscope illumination device of the second embodiment in the endoscope apparatus of FIG. 15.

In contrast with the first embodiment in which the handling section 120 is connected to the control box 150 by the connection cable 140, the endoscope apparatus of the present embodiment does not include a connection cable, the endoscope 270 is a wireless endoscope, and signals are wirelessly transmitted between the handling section 120 and the control box 280. Thus, the control box 280 is provided with a wireless transmission section 282.

Adoption of wireless transmission causes the configuration of the endoscope illumination device different from that of the first embodiment. Specifically, the LD section 210, LD drive circuit 14, optical coupler 16, PD section 230, detection circuit 22, and optical fibers 24 and 28, etc., which are provided within the control box 150 in the first embodiment, are contained in the handling section 120. Furthermore, a battery 272 and an endoscope side wireless transmission substrate 274 are provided within the handling section 120. In addition, a control box side wireless transmission substrate 284 is provided within the control box 280. Signals are wirelessly transmitted between the endoscope side wireless transmission substrate 274 and the control box side wireless transmission substrate 284.

Without the connection cable, the present embodiment can increase convenience, for example, enables change of a posture/position of the endoscope 270 without being pulled by the connection table, and enables a free layout unrestricted by the connection cable, when the endoscope 270 is used.

Third Embodiment

Next, a third embodiment will be described with reference to FIGS. 17 to 19. In those figures, the same members as those shown in FIGS. 1 to 16 are assigned the same reference numerals as those shown in FIGS. 1 to 16, and detailed descriptions thereof are omitted. Hereinafter, only points different from the first and second embodiments will be described. Namely, the parts not described below are the same as those in the first and second embodiments.

(LD/PD Section 310)

Figure 17:
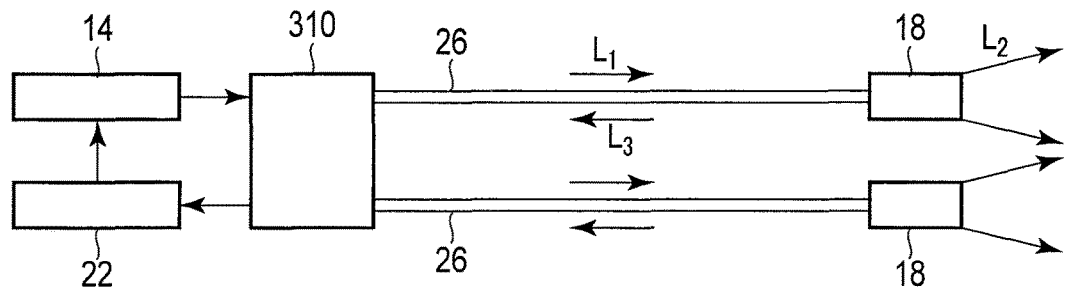
FIG. 17 schematically shows a general configuration of an endoscope illumination device of a third embodiment.

FIG. 17 schematically shows a general configuration of the endoscope illumination device of the third embodiment. In contrast with the first and second embodiments in which the LD section 12 and 210 is separated from the PD section 20 and 230, the endoscope illumination device 300 of the present embodiment includes an LD/PD section 310 on which an LD element and PD element are mounted in one package, instead of the LD section 12 and 210, the optical coupler 16, the PD section 20 and 230, and the optical fibers 24 and 28.

FIG. 18 shows a configuration of the LD/PD section 310 of the third embodiment. The LD/PD section 310 includes an LD element 312 that emits laser light with a wavelength of 445 nm, an LD element 314 that emits laser light with a wavelength of 405 nm, a collimate lens 316 that collimates a beam of laser light from the LD element 312, a collimate lens 318 that collimates a beam of laser light from the LD element 314, a half mirror 320 that combines and splits laser light from the LD element 312 and laser light from the LD element 314, a total reflection mirror 322 that deflects laser light from the half mirror 320, a 1% reflection mirror 324 that reflects 1% of laser light from the half mirror 320, a 1% reflection mirror 326 that reflects 1% of laser light reflected by the total reflection mirror 322, an LD monitor PD element 332 provided on a reflection light path of 1% reflection mirror 324, an LD monitor PD element 334 provided on a reflection light path of 1% reflection mirror 326, a dichroic mirror 328 that transmits laser light from 1% reflection mirror 324 and reflects return light, a dichroic mirror 330 that transmits laser light from 1% reflection mirror 326 and reflects return light, a lens 340 that converges laser light from dichroic mirror 328 to cause it to enter the optical fiber 26, a lens 342 that converges laser light from dichroic mirror 330 to cause it to enter the optical fiber 26, a return light PD element 336 provided on an optical path of return light reflected by dichroic mirror 328, and a return light PD element 338 provided on an optical path of return light reflected by dichroic mirror 330. The dichroic mirrors 328 and 330 are designed to transmit light with wavelengths of 445 nm and 405 nm and reflect light with a wavelength of 450 nm.

A beam of laser light with a wavelength of 445 nm, which is emitted from the LD element 312, is collimated by collimate lens 316 and enters the half mirror 320. A beam of laser light with a wavelength of 405 nm, which is emitted from the LD element 314, is collimated by collimate lens 318 and enters the half mirror 320. The beams of laser light with both wavelengths that have entered the half mirror 320 are split into two beams at a fifty-fifty branching ratio by the half mirror 320. Namely, of the laser light with both wavelengths that have entered the half mirror 320, components of about a half of the light quantity are transmitted through the half mirror 320, and components of approximately the other half of the light quantity are reflected by the half mirror 320. As a result, two split beams each equally include laser light with a wavelength of 445 nm and laser light with a wavelength of 405 nm. After that, approximately 1% of the components of laser light are reflected by the 1% reflection mirrors 324 and 326, and the reflected laser light enters the LD monitor PD elements 332 and 334. Laser light that have been transmitted through the 1% reflection mirrors 324 and 326 are transmitted through the dichroic mirrors 328 and 330, are converged by the lens 340 and 342, and enter the optical fibers 26. Components of laser light that have entered the two optical fibers 26 are guided to the distal end units 18 by the optical fibers 26. Parts of laser light that have entered the distal end units 18 are wavelength-converted by the fluorescent substances in the distal end units 18, and fluorescent light are emitted. Components of return light from the distal end units 18 are guided by the optical fibers 26 to the LD/PD section 310. Beams of return light radiated from the optical fibers 26 are collimated by the lenses 340 and 342, reflected by the dichroic mirrors 328 and 330, branched from the optical path of excitation light, and enter the return light PD elements 336 and 338.

A feature of the LD/PD section 310 is its significant miniaturization possibility. In general, LD elements and PD elements are distributed as a CAN package, and have a size of 5 mm in diameter. If such CAN packages corresponding in number to elements to be used are combined, the LD/PD section 310 has an extremely large size as the LD/PD section 310 is multi-functionalized. Use of a PKG on which LD and PD elements are integrated/mounted in units of elements enables keeping the module small even if the LD/PD section 310 is multi-functionalized. The LD/PD section is mounted in the handling section 120 in the endoscope 360 as will be described later; therefore, such a small module has high value added. Furthermore, accuracy of failure determination can be improved as described in the second embodiment by adding a branching mirror on an optical path of return light and separately measuring fluorescent light components and excitation light components in the return light.

(Failure Determination)

Since the number of mounted PD elements is larger in the present embodiment than in the first embodiment, the failure determination has higher flexibility. Specifically, first of all, LD monitor PD elements 332 and 334 are added. When a measurement value of the LD monitor PD element 332 or 334 is an unexpected value, the failure part can be narrowed down to the LD drive circuit 14, LD elements 312 and 314, and mirrors 320, 322, 324, and 326 from the LD elements 312 and 314 to the LD monitor PD elements 332 and 334. Moreover, since return light from each distal end unit 18 is individually measured by the return light PD element 336 or 338, which of two lights a failure has occurred in can be determined based on which of the return light PD elements 336 and 338 outputs an unexpected measurement value. In addition, the failure condition in the distal end unit 18 can be estimated by adding a structure that separates excitation light components from fluorescent light components of return light as shown in FIG. 13, as described above.

(Configuration for Mounting in Endoscope)

A configuration for mounting the endoscope illumination device of the present embodiment in an endoscope will be described. FIG. 19 shows a configuration for mounting the endoscope illumination device of the third embodiment in the endoscope apparatus of FIG. 15.

In the configuration for mounting in the endoscope apparatus, the endoscope 360 of the present embodiment has the same configuration as the wireless endoscope 270 as described in the second embodiment, except that the LD/PD section 310 is mounted instead of the LD section and the PD section.

CONCLUSION

Described above are three embodiments; however, the numbers of LD elements or PD elements, their PKG forms, the types and stack structures of fluorescent substances, the end face shapes of the optical fibers or fluorescent substances, types of the optical fibers, configurations for mounting in an endoscope, etc. of those embodiments may be used in combination without departing from the spirit of the present invention.

Additional advantages and modifications will readily occur to those skilled in the art. Therefore, the invention in its broader aspects is not restricted to the specific details and representative embodiments shown and described herein. Accordingly, various modifications may be made without departing from the spirit or scope of the general inventive concept as defined by the appended claims and their equivalents.

What is claimed is:

1. An endoscope illumination device, comprising:
a light source that outputs primary light;
a light guide that includes a first end face from which the primary light is radiated, and guides the primary light;
a light converter that is disposed to face the first end face, includes a second end face that the primary light enters, converts part of the primary light into secondary light; and
a holder that holds the light guide and the light converter so that an incident angle of the secondary light that is radiated from a point of intersection of the second end face and an optical axis of the light guide on the first end face and enters the first end face is equal to or larger than an acceptance angle (NA) of the light guide.

2. The endoscope illumination device according to claim 1, wherein, where a radius of a light guiding path cross section of the light guide is d, the acceptance angle of the light guide is NA, a refractive index of a medium between the first end face and the second end face is n, and a distance between the first end face and the second end face is L, the distance L between the first end face and the second end face satisfies $$L \leq \frac{d \times n \times \sqrt{1 - \left(\frac{NA}{n}\right)^2}}{NA}$$

3. The endoscope illumination device according to claim 1, further comprising an interval keeping member that defines the distance between the first end face and the second end face.

4. The endoscope illumination device according to claim 3, wherein the interval keeping member is a transparent member interposed between the light guide and the light converter.

5. The endoscope illumination device according to claim 3, wherein the holder includes a light guide holding hole into which the light guide is inserted and a light converter holding hole into which the light converter is inserted, the light guide holding hole communicates with the light converter holding hole, and the light converter holding hole has a tapered shape in which a hole diameter gradually increases from the light guide holding hole side.

6. The endoscope illumination device according to claim 5, wherein the first end face inserted into the holder is in the light converter holding hole.

7. The endoscope illumination device according to claim 1, wherein a transparent member is filled between the first end face and the second end face, the transparent member being optically transparent with respect to the primary light and the secondary light.

8. The endoscope illumination device according to claim 7, wherein
the first end face is convex, and a refractive index of the transparent member is lower than a refractive index of the light guide, or
the first end face is concave, and the refractive index of the transparent member is higher than the refractive index of the light guide.

9. The endoscope illumination device according to claim 7, wherein
the second end face is convex, and a refractive index of the transparent member is lower than a refractive index of the light converter, or
the second end face is concave, and the refractive index of the transparent member is higher than the refractive index of the light converter.

10. The endoscope illumination device according to claim 1, wherein the light guide is a multi-mode optical fiber configured to guide light in multiple modes.

11. The endoscope illumination device according to claim 10, wherein the optical fiber includes a core and a clad covering an outer peripheral cylindrical surface of the core, and a diameter of the clad is 1.2 times a diameter of the core or less.

12. The endoscope illumination device according to claim 10, wherein the optical fiber is a double-clad fiber including a core, a primary clad covering an outer peripheral cylindrical surface of the core, and a secondary clad covering an outer peripheral cylindrical surface of the primary clad.

13. The endoscope illumination device according to claim 12, wherein the primary light is guided in the core, and the secondary light is guided in the core and the primary clad.

14. The endoscope illumination device according to claim 10, wherein the optical fiber is an optical fiber including a core, a clad covering an outer peripheral cylindrical surface of the core, and a metal reflection film covering an outer peripheral cylindrical surface of the clad, and the metal reflection film has reflectivity with respect to both the primary light and the secondary light.

15. The endoscope illumination device according to claim 14, wherein the primary light is guided in the core, and the secondary light is guided in the core and the clad.

16. The endoscope illumination device according to claim 1, wherein the light converter is columnar, and has such a diameter as to provide an area allowing all the primary light radiated from the first end face to be applied to the light converter.

17. The endoscope illumination device according to claim 16, wherein the light converter includes a fluorescent substance.

18. The endoscope illumination device according to claim 1, further comprising a branching member that splits, from the primary light, return light guided by the light guide opposite in direction to travel of the primary light.

19. The endoscope illumination device according to claim 18, wherein the branching member is a dichroic mirror or an optical coupler.

20. The endoscope illumination device according to claim 18, further comprising a detection section that detects a light quantity of the return light guided by the light guide opposite in direction to travel of the primary light.

21. The endoscope illumination device according to claim 20, further comprising a control section that controls the light source based on the light quantity of the return light.

22. The endoscope illumination device according to claim 21, wherein the control section makes an output light quantity of the light source zero when the control section determines that a failure has occurred based on a detection result of the light quantity of the return light.

23. The endoscope illumination device according to claim 21, wherein the control section makes an output light quantity of the light source lower than in normal use when the control section determines that a failure has occurred based on a detection result of the light quantity of the return light.

24. The endoscope illumination device according to claim 1, wherein the holder includes a light guide holding hole into which the light guide is inserted and a light converter holding hole into which the light converter is inserted, and the light guide holding hole communicates with the light converter holding hole, further comprising a transparent member provided in the light converter holding hole of the holder.

* * * * *